United States Patent
Cho et al.

(10) Patent No.: US 8,475,741 B2
(45) Date of Patent: Jul. 2, 2013

(54) DROPLET DISCHARGING DEVICE

(75) Inventors: Seongjin Cho, Asan (KR); Geunbae Lim, Pohang (KR); Intae Kim, Pohang (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/375,286

(22) PCT Filed: Sep. 14, 2010

(86) PCT No.: PCT/KR2010/006269
§ 371 (c)(1),
(2), (4) Date: Nov. 30, 2011

(87) PCT Pub. No.: WO2011/052889
PCT Pub. Date: May 5, 2011

(65) Prior Publication Data
US 2012/0219468 A1    Aug. 30, 2012

(30) Foreign Application Priority Data
Oct. 29, 2009   (KR) .................. 10-2009-0103654

(51) Int. Cl.
    *B01L 3/02* (2006.01)
(52) U.S. Cl.
    USPC ........... 422/521; 422/501; 422/509; 422/218; 73/863.32; 73/863.33; 73/864; 73/864.01; 73/864.02; 73/864.11; 73/864.13; 73/864.15; 73/864.16; 73/864.34

(58) Field of Classification Search
    USPC   422/521, 501, 509, 518, 63–68.1; 73/863.32, 73/863.33, 864, 864.01, 864.02, 864.03, 73/864.11, 864.13, 864.14, 864.15, 864.16, 73/864.34, 864.35; 436/174, 180
    See application file for complete search history.

(56) References Cited

U.S. PATENT DOCUMENTS

| | | | |
|---|---|---|---|
| 3,804,108 A * | 4/1974 | Ferrari ........................ | 137/112 |
| 5,013,529 A * | 5/1991 | Itoh .............................. | 422/511 |
| 5,158,748 A * | 10/1992 | Obi et al. .................... | 422/511 |
| 5,316,954 A * | 5/1994 | Hupe et al. .................. | 436/89 |
| 5,330,717 A * | 7/1994 | Berteloot et al. ............ | 422/68.1 |
| 5,525,298 A * | 6/1996 | Anami .......................... | 422/63 |
| 5,558,838 A * | 9/1996 | Uffenheimer ................ | 422/510 |
| 6,495,106 B1 * | 12/2002 | Kalra et al. .................. | 422/510 |

(Continued)

FOREIGN PATENT DOCUMENTS

| | | |
|---|---|---|
| JP | 57-199857 | 12/1982 |
| JP | 61-178440 | 11/1986 |

(Continued)

*Primary Examiner* — Brian R Gordon
(74) *Attorney, Agent, or Firm* — Lexyoume IP Meister, PLLC.

(57) ABSTRACT

Provided is a droplet discharging device that can precisely dispense large flow rate of droplets and small flow rate of droplets selectively. The droplet discharging device according to the present invention includes a pneumatic discharger for discharging a droplet having a first flow rate, and an electronic pipette for discharging or sucking a droplet having a second flow rate equal to or smaller than the first flow rate. The pneumatic discharger includes, i) a storage chamber for storing a liquid, ii) an air tank connected to the storage chamber through a first air pipe and supplying compressed air to the storage chamber to push the liquid of the storage chamber outside, and iii) a first nozzle connected to the storage chamber through the liquid pipe and receiving the liquid pushed out of the storage chamber to discharge droplets.

13 Claims, 6 Drawing Sheets

U.S. PATENT DOCUMENTS

| | | | |
|---|---|---|---|
| 6,521,187 B1* | 2/2003 | Papen | 422/504 |
| 7,160,511 B2* | 1/2007 | Takahashi et al. | 422/504 |
| 7,491,548 B2* | 2/2009 | Quine et al. | 436/177 |
| 8,241,590 B2* | 8/2012 | Harada et al. | 422/521 |
| 8,296,088 B2* | 10/2012 | Roth et al. | 702/85 |
| 2002/0064482 A1* | 5/2002 | Tisone et al. | 422/100 |
| 2002/0064880 A1* | 5/2002 | Merten et al. | 436/43 |
| 2004/0077101 A1* | 4/2004 | Tegeler et al. | 436/174 |
| 2006/0263250 A1* | 11/2006 | Blouin et al. | 422/63 |
| 2007/0155019 A1* | 7/2007 | Johnson et al. | 436/180 |
| 2008/0314450 A1* | 12/2008 | Hawker et al. | 137/2 |
| 2009/0074614 A1* | 3/2009 | Ohga et al. | 422/67 |
| 2010/0173394 A1* | 7/2010 | Colston et al. | 435/287.2 |

FOREIGN PATENT DOCUMENTS

| | | |
|---|---|---|
| JP | 07-260799 | 10/1995 |
| JP | 08-146012 | 6/1996 |
| JP | 10-114394 | 5/1998 |
| JP | 2001-058132 | 3/2001 |
| JP | 2003-033707 | 2/2003 |
| JP | 2003-075305 | 3/2003 |
| JP | 2004-354070 | 12/2004 |
| JP | 2006-284426 | 10/2006 |
| JP | 2009-125656 | 6/2009 |
| KR | 10-2009-0108918 | 10/2009 |

* cited by examiner

DROPLET DISCHARGING DEVICE

TECHNICAL FIELD

The present invention relates to a droplet discharging device, and more particularly, to a droplet discharging device that can precisely dispense large flow rate of droplets and small flow rate of droplets selectively.

BACKGROUND ART

A droplet discharging device discharges a solution by the unit of a very small droplet (waterdrop) on a target such as a substrate. The droplet discharging device is widely used in a wide industrial field and recently, as the bioindustry and mechanical engineering are combined, researches on a droplet discharging device for bio equipment are being actively carried out.

A droplet discharging device for bio equipment of the related art generally has a simple structure using an electronic pipette. By using the droplet discharging device equipped with the electronic pipette, it is possible to easily dispense small flow rate of droplets with high reproducibility.

However, it is difficult to selectively precisely dispense small flow rate of droplets and large flow rate of droplets by the droplet discharging device of the related art equipped with the electronic pipette. In addition, the electronic pipette has a disadvantage in that because the electronic pipette dispenses medicine while being contacted with a target material, a nozzle tip needs to be replaced after a single usage.

DISCLOSURE

Technical Problem

The present invention has been made in an effort to provide a droplet discharging device having advantages of precisely dispensing large flow rate of droplets and small flow rate of droplets selectively.

Technical Solution

An exemplary embodiment of the present invention provides a droplet discharging device, including: a pneumatic discharger for discharging a droplet having a first flow rate, and an electronic pipette for discharging or sucking a droplet having a second flow rate equal to or smaller than the first flow rate. The pneumatic discharger may include i) a storage chamber for storing a liquid, ii) an air tank connected to the storage chamber through a first air pipe and supplying compressed air to the storage chamber to push the liquid of the storage chamber outside, and iii) a first nozzle connected to the storage chamber through a liquid pipe and receiving the liquid pushed out of the storage chamber to discharge droplets.

The pneumatic discharger may further include a regulator installed at the first air pipe between the air tank and the storage chamber to adjust the pressure of the compressed air.

The storage chamber may include i) a chamber main body having a sealing structure and connected to the first air pipe; and ii) a storage container positioned inside the chamber main body, storing the liquid, and forming an opened end at an upper portion. A portion of the liquid pipe may penetrate the chamber main body and be extended inside the storage container via the opened end.

The pneumatic discharger may further include i) a pinch valve installed at the liquid pipe between the storage chamber and the first nozzle to control opening and closing of the liquid pipe, ii) a precision flowmeter installed at the liquid pipe between the pinch valve and the first nozzle to detect the flow rate of the dispensed liquid, and iii) a display unit receiving flow rate information of the liquid from the precision flowmeter and displaying the flow rate information.

The first nozzle may include i) a nozzle tip receiving the liquid from the liquid pipe and discharging droplets by opening one end of the nozzle tip; and ii) a housing surrounding an upper portion of the nozzle tip while being spaced apart from the opened end of the nozzle tip and forming an injection hole injecting the compressed air toward the opened end of the nozzle tip.

The pneumatic discharger may further include i) a second air pipe connecting the air tank with the housing to supply the compressed air to the housing and ii) a solenoid valve installed at the second air pipe between the air tank and the housing to control the flow of the compressed air.

The injection hole may have a diameter larger than an exterior diameter of the nozzle tip and the nozzle tip may penetrate the center of the injection hole to provide a space with uniform widths along a circumferential direction of the nozzle tip.

The housing may form a passage where the compressed air flows inside the housing and the passage may be connected to the injection hole to inject the compressed air to the space of the injection hole surrounding the nozzle tip.

The electronic pipette may include i) a syringe provided with a cylinder and a piston, ii) a driving motor coupled with the piston to linearly move the piston, and iii) a nozzle tip installed at an end of the cylinder and discharging or sucking the liquid according to the movement of the piston.

The first flow rate may increase from a minimum of 1 μl by 0.1 μl unit and the second flow rate may increase from a minimum of 0.1 μl by 0.02 μl unit.

Advantageous Effects

According to the exemplary embodiment of the present invention, the droplet discharging device can precisely dispense droplets having various flow rates by selectively driving any one of the pneumatic discharger and the electronic pipette. Further, since the pneumatic discharger discharges the droplet without being contacted with a target material, the pneumatic discharger can be used in a difficult situation to be contacted with the target material and it is not necessary to replace the nozzle tip whenever using the pneumatic discharger. The pneumatic discharger can precisely dispense droplets at a flow rate of a minimum of 1 μl.

MODE FOR INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
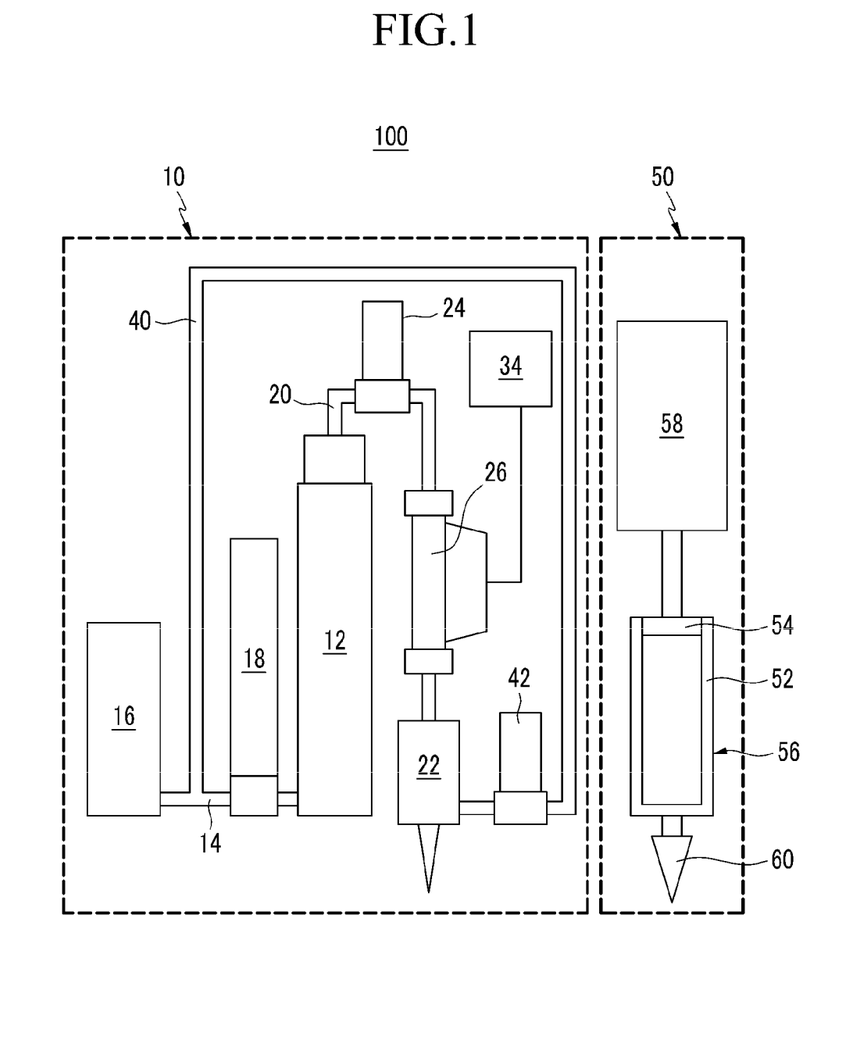
FIG. 1 is a schematic diagram of a droplet discharging device according to an exemplary embodiment of the present invention.

FIG. 1 is a schematic diagram of a droplet discharging device according to an exemplary embodiment of the present invention.

Referring to FIG. 1, a droplet discharging device 100 according to the exemplary embodiment of the present invention includes a pneumatic discharger 10 for discharging a droplet having a first flow rate and an electronic pipette 50 for discharging or sucking a droplet having a second flow rate equal to or smaller than the first flow rate. The pneumatic discharger 10 for uniformly dispensing droplets having a large flow rate as compared to the electronic pipette 50, pushes a liquid inside a storage chamber 12 by the pressure of compressed air to discharge a droplet.

The pneumatic discharger 10 includes a storage chamber 12 storing a liquid (medicine), an air tank 16 connected to the storage chamber 12 through a first air pipe 14, a regulator 18 installed at the first air pipe 14 between the air tank 16 and the storage chamber 12, a first nozzle 22 connected to the storage chamber 12 through a liquid pipe 20, a pinch valve 24 installed at the liquid pipe 20 between the storage chamber 12 and the first nozzle 22, and a precision flowmeter 26 installed at the liquid pipe 20 between the pinch valve 24 and the first nozzle 22.

The air tank 16 serves to supply compressed air to the storage chamber 12 through the first air pipe 14 to push the liquid inside the storage chamber 12 to the outside of the storage chamber 12. In this case, the regulator 18 installed at the first air pipe 14 adjusts the pressure of the compressed air to allow the compressed air having the uniform pressure to be supplied to the storage chamber 12.

Figure 2:
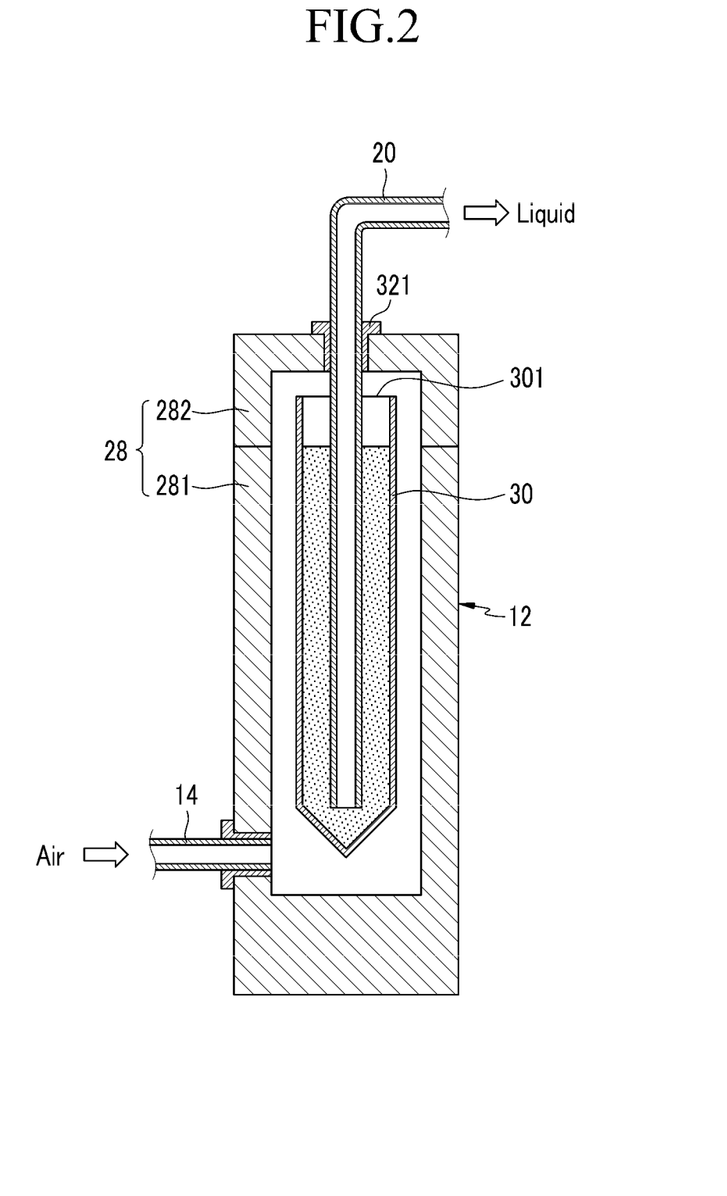
FIG. 2 is a cross-sectional view of a storage chamber of the droplet discharging device shown in FIG. 1.

FIG. 2 is a cross-sectional view of a storage chamber of the droplet discharging device shown in FIG. 1.

Referring to FIG. 2, the storage chamber 12 includes a chamber main body 28 having a sealing structure and a storage container 30 positioned inside the chamber main body 28. The chamber main body 28 is connected to the first air pipe 14 and the storage container 30 is connected to the liquid pipe 20.

The chamber main body 28 may be constituted by a combined structure of a first main body 281 including a bottom portion and sidewalls and a second main body 282 detachably coupled with a top portion of the first main body 281 to serve as a lid. The first main body 281 and the second main body 282 are tightly sealed in coupling to prevent the compressed air inside the chamber main body 28 from leaking outside. An end of the first air pipe 14 may be connected to a lower portion of the first main body 281.

The storage container 30 is disposed apart from an inner wall of the chamber main body 28 at a predetermined distance and stores a liquid (medicine) therein. The storage container 30 forms an open end 301 at an upper portion to allow the pressure of the compressed air to be applied to the liquid. A portion of the liquid pipe 20 penetrates the second main body 282 and is extended inside the storage container 30 via the opening end 301. To this end, the second main body 282 forms an opening through which the liquid pipe 20 passes and a sealing gasket 321 is installed around the liquid pipe 20 to prevent the leakage of the compressed air.

In the above-described configuration, when the compressed air is supplied to the chamber main body 28, the air pressure inside the chamber main body 28 changes to be different from the external atmospheric pressure. By the pressure difference, the liquid of the storage container 30 is pushed out of the chamber main body 28 through the liquid pipe 20 and the first nozzle 22 receives the pushed liquid to discharge the liquid in a droplet (waterdrop) form.

Referring to FIG. 1, the pinch valve 24 installed at the liquid pipe 20 controls opening and closing of the liquid pipe 20 to determine whether to dispense the liquid. The precision flowmeter 26 detects a flow rate of the liquid flowing through the liquid pipe 20 when the liquid pipe 20 is opened by operation of the pinch valve 24 and allows a user to check the flow rate of the dispensed liquid. To this end, the pneumatic discharger 10 further includes a display unit 34 for displaying discharge flow rate information.

The first nozzle 22 in the present exemplary embodiment has a structure in which the droplet is not dropped only by the pressure of the liquid, but the compressed air is injected toward the droplet from an upper portion of the droplet. In a structure in which the droplet is dropped only by the pressure of the liquid, it is not possible to reduce the size of the droplet below a predetermined level.

Therefore, in the droplet discharging device 100 of the present exemplary embodiment, the first nozzle 22 has a function to extremely precisely control the flow rate of the droplet discharged from the pneumatic discharger 10 by reducing the size of the droplet as necessary to reduce the minimum value of the first flow rate, as well as a basic function to discharge the droplet having the larger flow rate compared to the electronic pipette 50.

Figure 3:
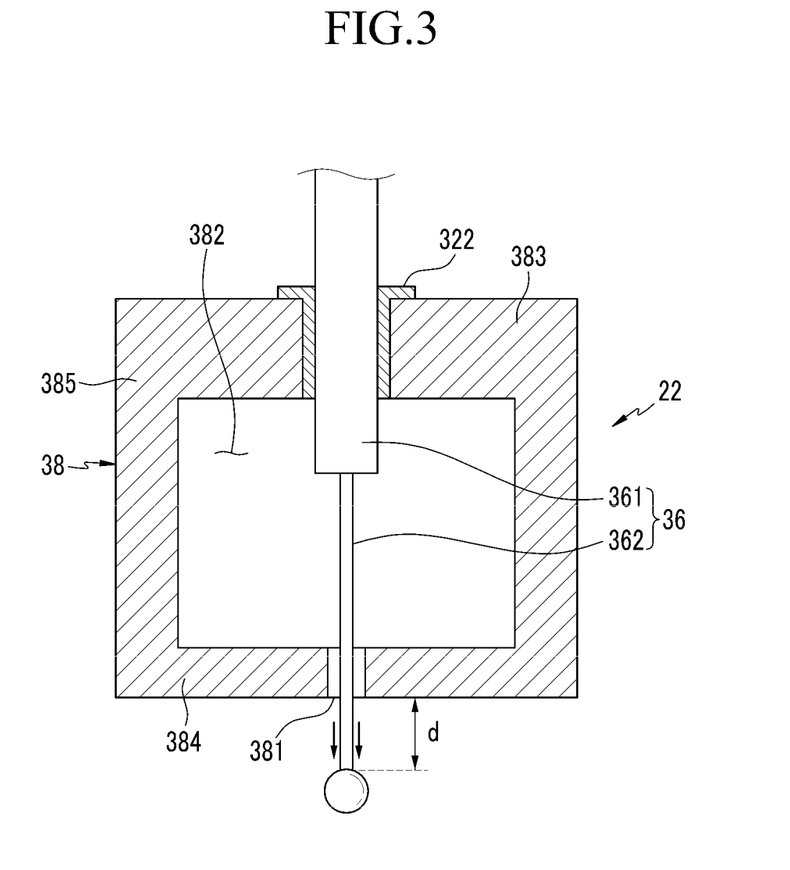
FIG. 3 is a cross-sectional view of a first nozzle of the droplet discharging device shown in FIG. 1.

FIG. 3 is a cross-sectional view of a first nozzle of the droplet discharging device shown in FIG. 1.

Referring to FIGS. 1 and 3, the first nozzle 22 includes a nozzle tip 36 connected to the liquid pipe 20 and discharging the droplet by opening a lower end and a housing 38 surrounding an upper portion of the nozzle tip 36 while being spaced apart from the opened end of the nozzle tip 36 and forming an injection hole 381.

The housing 38 forms an inner space surrounding a portion of the nozzle tip 36 and the inner space is configured to serve as a passage 382 through which the compressed air supplied inside the housing 36 is circulated. The nozzle tip 36 may be constituted by an upper nozzle 361 connected to the liquid pipe 20 and having a first diameter and a lower nozzle 362 connected to the upper nozzle 361 and having a second diameter smaller than the first diameter.

The housing 38 may include a first horizontal part 383 surrounding the upper nozzle 361 with the sealing gasket 322 interposed therebetween, a second horizontal part 384 disposed below the first horizontal part 383 and forming the injection hole 381 through which the lower nozzle 362 passes, and a vertical part 385 connecting the first horizontal part 383 and the second horizontal part 384. The second horizontal part 384 is disposed above the opened end of the lower nozzle 362 at a predetermined distance d (see FIG. 3) along a direction perpendicular (vertical direction of the figure) to the ground. Therefore, the injection hole 381 is also disposed above the opened end of the lower nozzle 362.

The injection hole 381 has a diameter larger than an exterior diameter of the lower nozzle 362 and the second horizontal part 384 maintains the uniform distance from the lower nozzle 362 along a circumferential direction of the lower nozzle 362. That is, as the lower nozzle 362 penetrates the center of the injection hole 381, a space through which the compressed air is discharged is formed at the uniform distance from a circumference of the lower nozzle 362. The passage 382 inside the housing 38 is connected to the injection hole 381 to discharge the compressed air through the injection hole 381.

The droplet discharging device 100 includes a second air pipe 40 connecting the air tank 16 with the housing 38 in order to supply the compressed air to the housing 38. The end of the second air pipe 40 may be connected to the vertical part 385 of the housing 38. Further, a solenoid valve 42 is installed at the second air pipe 40 between the air tank 16 and the housing 38 to control the passing of the compressed air.

When the liquid is supplied to the nozzle tip 36 through the liquid pipe 20, a droplet as a liquid drop is formed at an end of the lower nozzle 362. In this case, because the surface tension of the droplet is larger than gravity applied to the droplet, the droplet does not drop downward and remains at the end of the lower nozzle 362. Further, when the compressed air is supplied to the passage 382 inside the housing 38 through the second air pipe 40, the compressed air is injected through the injection hole 381 surrounding the lower nozzle 362.

The direction where the compressed air is injected corresponds to a direction where the droplet is pushed and dropped downward and as the injection hole 381 is formed to be continuously linked along the circumferential direction of the lower nozzle 362, the force applied to the droplet is uniformly distributed. As a result, the uniform force is applied to the droplet remaining at the end of the lower nozzle 362 downward.

If the force applied by the compressed air is unevenly distributed to one side, the droplet falls not vertically but slantly, such that it is difficult to accurately discharge the droplet at a predetermined position. However, since in the present exemplary embodiment, the space with the uniform width along the circumferential direction of the lower nozzle 362 is provided by forming the injection hole 381, it is possible to uniformly distribute the force applied to the droplet. Accordingly, it is possible to exactly discharge the droplet at the predetermined position by dropping the droplet vertically.

Figure 4:
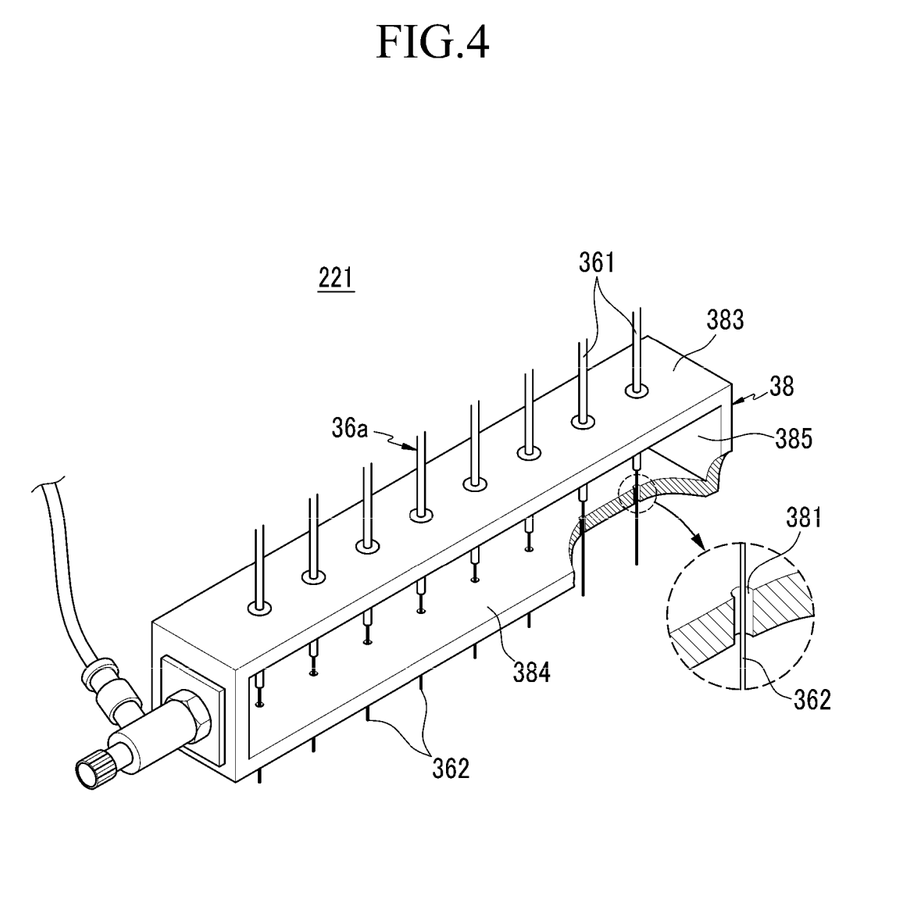
FIG. 4 is a partially cut-away perspective view illustrating another exemplary embodiment of a first nozzle of the droplet discharging device shown in FIG. 1.

Meanwhile, FIG. 3 shows that one nozzle tip 36 and one injection hole 381 are provided in the first nozzle 22, but the nozzle tip and the injection hole may be provided in plural. FIG. 4 is a partially cut-away perspective view illustrating another exemplary embodiment of a first nozzle of the droplet discharging device shown in FIG. 1. In FIG. 4, one of four vertical parts of the housing is omitted for convenience.

Referring to FIG. 4, a plurality of nozzle tips 36a are arranged in parallel at a distance from each other in the first nozzle 221 and injection holes 381 are formed at a second horizontal part 384 of the housing to correspond to each of the nozzle tips 36a. The plurality of nozzle tips 36a are constituted by branch pipes branched from the liquid pipe and receive equal amounts of liquid to form the droplet at the lower end and then discharge the droplet downward.

Referring to FIG. 1, the electronic pipette 50 includes a syringe 56 provided with a cylinder 52 and a piston 54 and storing the liquid, a driving motor 58 coupled with the piston 54 and driving the piston 54 to push the liquid, and a second nozzle 60 installed at the end of the cylinder 52 to discharge the liquid. The driving motor 58 may be a step motor and the liquid is pushed by operation of the driving motor 58 and the piston 54 to discharge the droplet to the second nozzle 60. In addition, the electronic pipette 50 sucks the liquid inside the syringe 56 through the second nozzle 60 when the piston 54 is driven in an opposite direction.

Since the droplet discharging device 100 configured as described above includes both the pneumatic discharger 10 and the electronic pipette 50, any one of the pneumatic discharger 10 and the electronic pipette 50 is selectively driven according to the discharge flow rate. Therefore, the droplet discharging device 100 can precisely dispense droplets having various flow rates and be easily applied to precision instruments in a variety of fields requiring the droplet-discharging as well as bio equipment.

Further, since the pneumatic discharger 10 discharges the droplet without being contacted with a target material, the pneumatic discharger 10 can be used in a difficult situation to be contacted with the target material (e.g., high temperature environment or use of damageable material) and it is not necessary to replace the nozzle tip 36 whenever using the pneumatic discharger 10. The first flow rate of the droplet discharged by the pneumatic discharger 10 may be in the range of 1 μl to the maximum storage capacity of the storage chamber 12 (e.g., 50 ml) and the pneumatic discharger 10 can adjust the first flow rate by 0.1 μl unit.

Since the electronic pipette 50 can dispense the droplet and suck the liquid, the electronic pipette has all the functions of delivering, distributing, and washing the medicine. Further, when the driving motor 58 is constituted by a precision motor, it is possible to precisely dispense the droplet at a minute flow rate of a minimum of 0.1 μl and the electronic pipette 50 can adjust the second flow rate by 0.02 μl unit.

Figure 5:
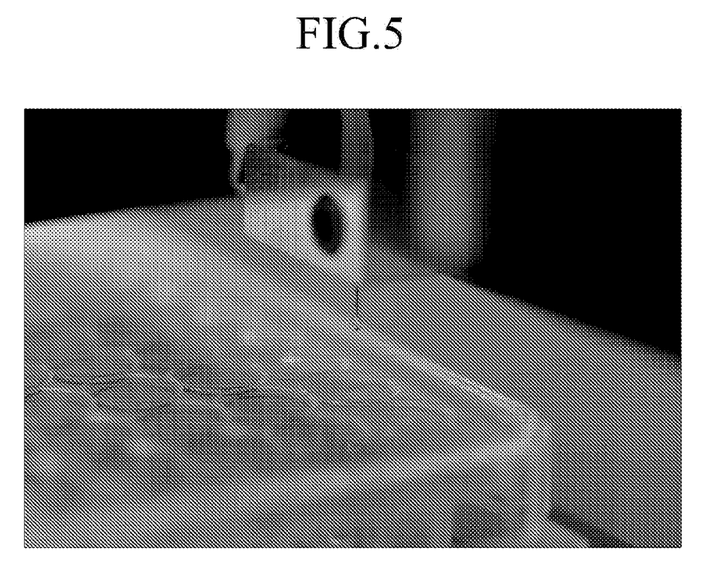
FIG. 5 is a photograph illustrating when a droplet is formed on a nozzle tip of a pneumatic discharger of the droplet discharging device according to an exemplary embodiment of the present invention.
Figure 6:
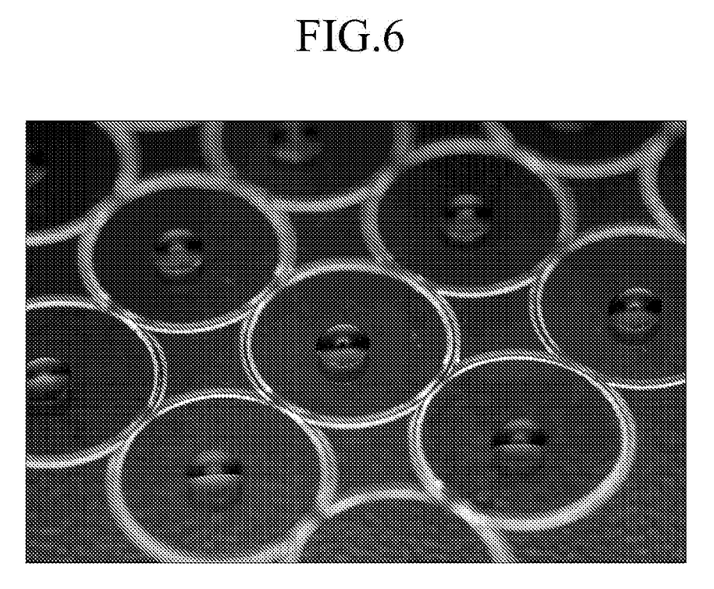
FIG. 6 is a photograph illustrating when droplets of 1 μl are dropped onto a microplate by using the pneumatic discharger shown in FIG. 5.

FIG. 5 is a photograph illustrating when a droplet is formed on a nozzle tip of a pneumatic discharger of the droplet discharging device according to an exemplary embodiment of the present invention and FIG. 6 is a photograph illustrating when droplets of 1 μl are dropped onto a microplate (96-well plate) by using the pneumatic discharger shown in FIG. 5. Referring to FIGS. 5 and 6, droplets of 1 μl are precisely dispensed onto the microplate at regular intervals by the pneumatic discharger.

Figure 7:
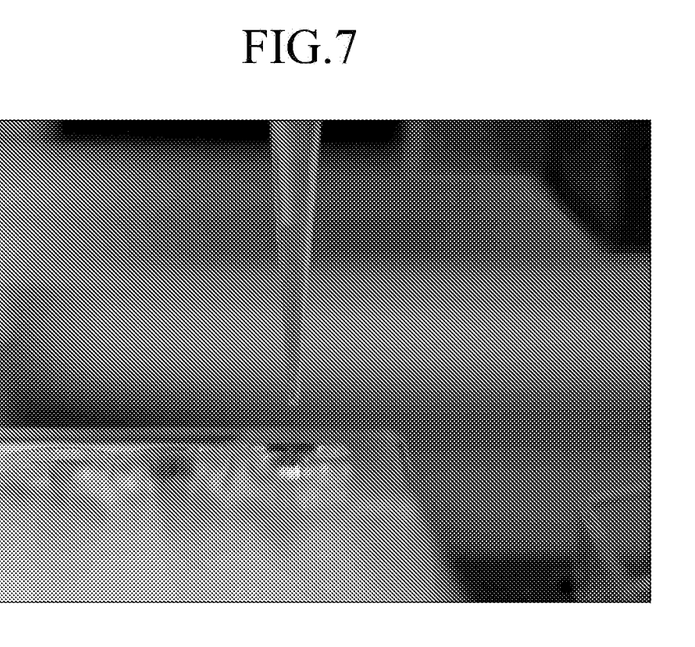
FIG. 7 is a photograph illustrating when liquid is sucked into a second nozzle of an electronic pipette of the droplet discharging device according to an exemplary embodiment of the present invention.
Figure 8:
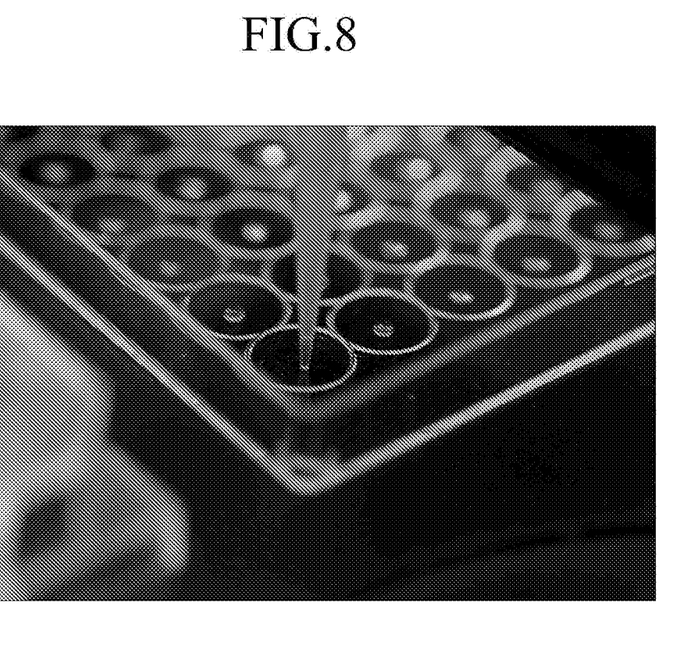
FIG. 8 is a photograph illustrating when droplets of 1 μl are dropped onto a microplate by using the electronic pipette shown in FIG. 7.

FIG. 7 is a photograph illustrating when a liquid is sucked into a second nozzle of an electronic pipette of the droplet discharging device according to an exemplary embodiment of the present invention and FIG. 8 is a photograph illustrating when droplets of 1 μl are dropped onto a microplate (96-well plate) by using the electronic pipette shown in FIG. 7. In the case where the electronic pipette dispenses the droplets after the nozzle tip is contacted with the target material, it is also possible to precisely dispense the droplets having the flow rate of less than 1 μl. FIGS. 7 and 8 show when droplets of 1 μl are dropped without the contact with the target material.

The liquid used in the tests of FIGS. 5 to 8 is deionized water.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A droplet discharging device, comprising:
 a pneumatic discharger for discharging a droplet having a first flow rate, and an electronic pipette for discharging or sucking a droplet having a second flow rate equal to or smaller than the first flow rate, wherein the pneumatic discharger includes a storage chamber for storing a liquid;

an air tank connected to the storage chamber through a first air pipe and supplying compressed air to the storage chamber to discharge the liquid of the storage chamber outside; and a first nozzle connected to the storage chamber through a liquid pipe and receiving the liquid pushed out of the storage chamber to discharge a droplet.

2. The droplet discharging device of claim 1, wherein:

the pneumatic discharger further includes a regulator installed at the first air pipe between the air tank and the storage chamber to adjust the pressure of the compressed air.

3. The droplet discharging device of claim 1, wherein:

the storage chamber includes a chamber main body having a sealing structure and connected to the first air pipe; and a storage container positioned inside the chamber main body, storing the liquid, and forming an opened end at an upper portion, and a portion of the liquid pipe penetrates the chamber main body and is extended inside the storage container via the opened end.

4. The droplet discharging device of claim 3, wherein:

the pneumatic discharger further includes a pinch valve installed at the liquid pipe between the storage chamber and the first nozzle to control opening and closing of the liquid pipe.

5. The droplet discharging device of claim 4, wherein:

the pneumatic discharger further includes a precision flowmeter installed at the liquid pipe between the pinch valve and the first nozzle to detect the flow rate of the dispensed liquid.

6. The droplet discharging device of claim 5, wherein:

the pneumatic discharger further includes a display unit receiving flow rate information of the liquid from the precision flowmeter and displaying the flow rate information.

7. The droplet discharging device of claim 1, wherein:

the first nozzle includes a nozzle tip receiving the liquid from the liquid pipe and discharging droplets by opening one end of the nozzle tip; and a housing surrounding an upper portion of the nozzle tip while being spaced apart from the opened end of the nozzle tip and forming an injection hole injecting the compressed air toward the opened end of the nozzle tip.

8. The droplet discharging device of claim 7, wherein:

the pneumatic discharger further includes a second air pipe connecting the air tank with the housing to supply the compressed air to the housing.

9. The droplet discharging device of claim 8, wherein:

the pneumatic discharger further includes a solenoid valve installed at the second air pipe between the air tank and the housing to control the flow of the compressed air.

10. The droplet discharging device of claim 7, wherein:

the injection hole has a diameter larger than an exterior diameter of the nozzle tip and the nozzle tip penetrates the center of the injection hole to provide a space with the uniform width along a circumferential direction of the nozzle tip.

11. The droplet discharging device of claim 10, wherein:

the housing forms a passage where the compressed air flows inside the housing and the passage is connected to the injection hole to inject the compressed air to the space of the injection hole surrounding the nozzle tip.

12. The droplet discharging device of claim 1, wherein:

the electronic pipette includes a syringe provided with a cylinder and a piston;

a driving motor coupled with the piston to linearly move the piston; and a nozzle tip installed at an end of the cylinder and discharging or sucking the liquid according to the movement of the piston.

13. The droplet discharging device of claim 1, wherein:

the first flow rate increases from a minimum of 1 µl/minute by 0.1 µl/minute and the second flow rate increases from a minimum of 0.1 µl/minute by 0.02 µl/minute.

* * * * *